United States Patent [19]

Shigematsu et al.

[11] 4,229,461

[45] Oct. 21, 1980

[54] FUNGICIDAL 6-(3,5-DICHLOROPHENYL)PERHYDROIMIDAZO[5,1-b]THIAZOLE DERIVATIVES

[75] Inventors: Taichiro Shigematsu, Machida; Kenji Yoshida, Yokohama; Makoto Nakazawa, Sagamihara; Hiroshi Kasugai, Yokohama; Masataka Tsuda, Machida, all of Japan

[73] Assignee: Mitsubishi Chemical Industries Limited, Tokyo, Japan

[21] Appl. No.: 49,620

[22] Filed: Jun. 18, 1979

[30] Foreign Application Priority Data

Jun. 30, 1978 [JP] Japan ................................. 53-79442
Sep. 20, 1978 [JP] Japan ................................. 53-115372

[51] Int. Cl.$^3$ ........................................... C07D 277/60
[52] U.S. Cl. ..................................... 424/270; 548/154
[58] Field of Search ................ 424/270; 548/154, 155

[56] References Cited

U.S. PATENT DOCUMENTS 3,671,534  6/1972  Houlihan et al. ..................... 548/154

FOREIGN PATENT DOCUMENTS 2604989  8/1976  Fed. Rep. of Germany .

OTHER PUBLICATIONS

C.A., vol. 62, p. 5263 (a), 1965.
C.A., vol. 63, p. 5269 (a), 1965.

*Primary Examiner*—Nicholas S. Rizzo
*Attorney, Agent, or Firm*—George A. Loud

[57] ABSTRACT

This invention relates to fungicidal novel derivatives of 6-(3,5-dichlorophenyl)perhydroimidazo[5,1-b]thiazole derivative. These compounds may be used for controlling fungal infection, especially in agriculture.

9 Claims, No Drawings

FUNGICIDAL 6-(3,5-DICHLOROPHENYL)PERHYDROIMIDAZO[5,1-b]THIAZOLE DERIVATIVES

BACKGROUND OF THE INVENTION

1. Field of the Invention

This invention relates to novel perhydroimidazothiazole derivatives. More particularly, it relates to 6-(3,5-dichlorophenyl) perhydroimidazo[5,1-b]thiazole-5,7-dions and 6-(3,5-dichlorophenyl)perhydroimidazo[5,1-b]thiazole-5-thion-7-ons, which are hydantoin derivatives and show excellent fungicidal activities.

2. Prior Art

A number of 3-substituted hydantoin-type compounds are known. In German Offenlegungsschrift No. 2 604 989, 1,5-alkylene-3-aryl hydantoin derivatives which are useful as a herbicides and/or a fungicides, are disclosed. Especially, 1,5-alkylene-3-(3,5-dichlorophenyl) hydantoin is known as a fungicide. Now, we found that novel hydantoin derivatives expressed by the formula (I) indicated below, i.e. 6-(3,5-dichlorophenyl)perhydroimidazo[5,1-b]thiazole-5,7-dions or 6-(3,5-dichlorophenyl) perhydroimidazo[5,1-b]thiazole-5-thion-7-ons, are very useful substances showing remarkable fungicidal effects on plant diseases.

SUMMARY OF THE INVENTION

This invention relates to 6-(3,5-dichlorophenyl)perhydroimidazo [5,1-b]thiazole compounds expressed by the formula

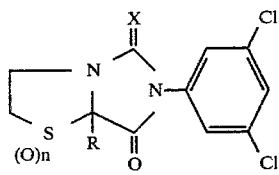

wherein R represents a hydrogen atom or an alkyl group of 1 through 4 carbon atoms, X represents an oxygen atom or a sulfur atom, and n is 0, 1 or 2. This invention also includes fungicidal compositions containing as their effective component the above 6-(3,5-dichlorophenyl)perhydroimidazo[5,1-b]thiazole compound expressed by the formula (I) and methods of controlling fungal infection on plants by applying the compounds and/or compositions to the plants. Further, this invention includes methods of preparing the compound expressed by the formula (I).

DESCRIPTION OF PREFERRED EMBODIMENTS

According to the present invention, there are provided 6-(3,5-dichlorophenyl)perhydroimidazo[5,1-b]thiazole compounds expressed by the formula

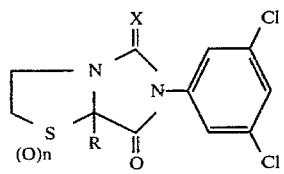

wherein R represents a hydrogen atom or an alkyl group of 1 through 4 carbon atoms, X represents an oxygen atom or a sulfur atom, and n is 0, 1 or 2.

The alkyl group may be methyl, ethy, propyl or butyl. All the compounds of the invention expressed by the formula (I) are novel and exhibit a powerful fungicidal efficacy against plant diseases but show little or no injury against plants per se. In addition, these compounds are low in toxicity against man and animals of fishes. The compounds of the invention show excellent efficacy on various diseases of vegetable, fruits-trees and rice, especially gray molds (*Botrytis cinerea Botrytis alli*), sclerotinia rots (*Sclerotinia sclerotiorum*), apple leaf spot (*Alternaria mali*), pear black spot (*Alternalia kikuchiana*), rice blast (*Pyricularia oryae*) and rice brown spot (*Cochliobolus myabeanus*).

Besides, the compounds of the invention show a high activity against fungi which are resistant to the chemicals (e.g. Benlate, Topsin-M, Polyoxin) commonly used in the agricultural field.

Among the instant compounds, the preferred compounds of the formula (I) are those in which X is an oxygen atom, R is a hydrogen atom or an alkyl group with 1 to 3 carbon atoms and n is 0, more preferably the compound of the formula (I) in which X is an oxygen atom, R is a hydrogen atom, methyl group or ethyl group and n is 0 in view of the fungicidal activity.

More preferred for their higher degree of fungicidal activity and ease of synthesis are the compounds 6-(3,5-dichlorophenyl)perhydroimidazo[5,1-b]thiazole-5,7-dion and 7a-methyl-6-(3,5-dichlorophenyl)perhydroimidazo[5,1-b]thiazole-5,7-dion.

The instant compounds of the formula (I) are prepared by intramolecular condensation of thiazolidine-2-carboxylic acid derivatives of the following formula (II).

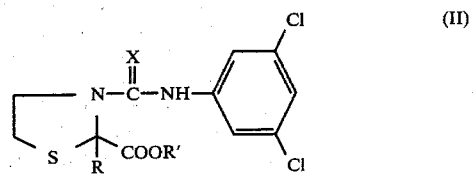

in which R represents a hydrogen atom or an alkyl group of 1 through 4 carbon atoms, X represents an oxygen atom or a sulfur atom, and R' represents a hydrogen atom or a lower alkyl group having 1 to 5 carbon atoms.

The compounds of the formula (II) can be prepared by reacting the thiazolidine-2-carboxylic acid which may be substituted in 2-position with an alkyl group of 1 to 4 carbon atoms or its lower alkyl ester and 3,5-dichlorophenylisocyanate or 3,5-dichlorophenylisothiocyanate. This can be expressed by a reaction formula as follows:

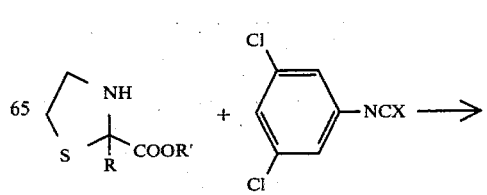

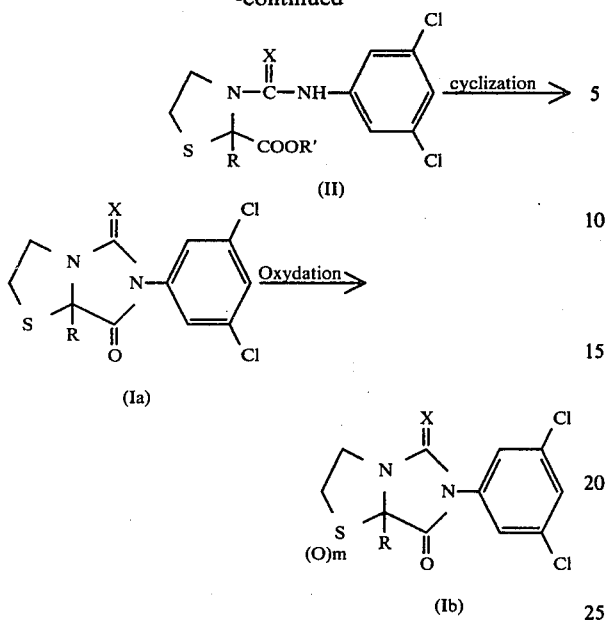

(in which formula R and X have the same meanings as defined in the foregoing formula (I), respectively, R' represents a hydrogen atom or a lower alkyl group 1 to 5 carbon atoms, m is 1 or 2).

When the lower alkyl esters of thiazolidine-2-carboxylic acid are used as the starting material, the esters are reacted with 3,5-dichlorophenylisocyanate or 3,5-dichlorophenylisothiocyanate in a solvent such as benzene, toluene, ether, dimethylformamide or the like to obtain 3-(3,5-dichlorophenylcarbamoyl)thiazolidine-2-carboxylic acid ester or 3-(3,5-dichlorophenylthiocarbamoyl) thiazolidine-2-carboxylic acid esters (where R'=a lower alkyl group in the formula (II)).

In the above reaction, continuation of the reaction after formation of the 3-substituted thiazolidine-2-carboxylic acid esters (where in the formula (II) R'=a lower alkyl group) may result, depending on the reaction conditions, to give intended 6-(3,5-dichlorophenyl)perhydroimidazo[5,1-b]thiazole-5,7-dions or 6-(3,5-dichlorophenyl)perhydroimidazo[5,1-b]thiazole-5-thion-7-ons expressed by the formula (Ia). From thiazolidine-2-carboxylic acids used as the starting material there can be obtained 3-(3,5-dichlorophenylcarbamoyl)thiazolidine-2-carboxylic acids or 3-(3,5-dichlorophenylthiocarbamoyl) thiazolidine-2-carboxylic acids (in the formula (II), R'=hydrogen atom) by suspending or dissolving the acids of the starting material in a mixed solvent of an organic solvent such as, for example, benzene, chlorobenzene, ether or dimethylformamide and water, reacting with 3,5-dichlorophenylisocyanate or 3,5-dichlorophenylisothiocyanate in the presence of an alkali such as caustic soda or caustic potash, and then neutralizing with a mineral acid such as hydrochloric acid or sulfuric acid.

Then the compounds of the formula (II) are condensed internally thereby converting into the intended 6-(3,5-dichlorophenyl) perhydroimidazo[5,1-b]thiazole-5,7-dions or 6-(3,5-dichlorophenyl) perhydroimidazo[5,1-b]thiazole-5-thion-7-ons (Ia). Usually, the compound is heated in the presence of a mineral acid such a hydrochloric acid or sulfuric acid or heated in acetic anhydride in the presence of an alkali metal salt of acetic acid such as sodium acetate. In these cases, condensation is otained is obtained by heating to above about 50° C., preferably to 80°–150° C., in the presence of an alcoholate of an alkali metal such as sodium alcoholate or potassium alcoholate in a lower alkanol such as ethanol or methanol. The resulting compounds are purified by conventional techniques such as recrystallization, chromatography, and the like. Further, 6-(3,5-dichlorophenyl)perhydroimidazo[5,1-b]thiazole-5,7-dion-1-oxides or -1,1-dioxides or 6-(3,5-dichlorophenyl) perhydroimidazo[5,1-b]thiazole-5-thion-7-on-1-oxides or -1,1-dioxides (Ib) can be obtained by dissolving the compounds (Ia) in a solvent such as methylene chloride and oxidizing with an oxidizing agent such as m-chloroperbenzoic acid or peracetic acid.

When applied as an agricultural fungicide, the compounds of the invention may be used as is but preferably are admixed with adjuvants for use in the form of an emulsion, a wettable powder, a dust or the like so as to effectively disperse the effective component upon application.

Suitable solvents which constitute one class of adjuvants for the fungicide of the invention are, for example, water, alcohols (such as methyl alcohol, ethyl alcohol, ethylene glycol and the like), ketones (such as acetone, methyl ethyl ketone, cyclohexanone and the like), ethers (such as ethyl ether, dioxane, cellosolves and the like), aliphatic hydrocarbons (such as kerosene, lamp oil, fuel oil and the like), aromatic hydrocarbons (such as benzene, toluene, xylene, solvent naphtha, methylnaphthalene and the like), halogenated hydrocarbons (such as dichloroethane, trichlorobenzene, carbon tetrachloride and the like), acid amides (such as dimethylformamide and the like), esters (such as ethyl acetate, butyl acetate, glycerine esters of aliphatic acids and the like), nitriles (such as acetonitrile and the like). These solvents may be used singly or in combination of two or more.

Suitable fillers are, for examle, mineral powders including clays such as kaolin, bentonite and the like, talcs such as talc, pyrophyllite and the like, mineral powders such as diatomaceous earth, white carbon, plant powders such as soy bean powder, CMC powder and the like. These may be used singly or in combinations of two or more.

A surface active agent may be used as a spreader, dispersant, emulsifier or penetrant. Examples of suitable surface active agents include nonionic active agents (such as polyoxyethylene alkylaryl ether, polyoxyethylene sorbitan monolaurate and the like), cationic active agents (such as alkyldimethylbenzylammonium chloride, alkylpyridinium chloride and the like), anionic active agents (such as alkylbenzene sulfonate, lignin sulfonate, higher alcohol sulfate), amphoteric surfactants (such as alkyldimethylbetaine, dodecylaminoethylglycine and the like). These surface active agents may be used singly or in combination depending on the purpose in end use.

When using the agricultural fungicide in the form of an emulsion, a formulated concentrate obtained by suitably mixing 10–50 parts of the compound of the invention, 10–80 parts of the solvent and 3–20 parts of the surface active agent is diluted with water to a predetermined level and applied in the usual manner, such as by spraying.

When using in the form of a wettable powder, 5–80 parts of the compound of the invention and 10–90 parts of the filler, and 1–20 parts of the surface active agent are mixed in suitable ratios and the mixture is then diluted with water, in a manner similar to the case of the emulsion, for subsequent use.

In the case of a dust, in general, 1-5 parts of the compound of the invention are uniformly mixed with 95-99 parts of a filler such as kaolin, bentonite, talc or the like and the mixture is then applied.

The agricultural fungicide according to the invention may be used by mixing with other active components which do not impede the fungicidal effect of the present component, e.g. other fungicides, insecticides, miticides and the like.

For foliage treatment, the fungicide of the invention is used in the amount of 50-500 l of a 250-1500 ppm of an active ingredient solution per 10 ares.

The present invention will now be described in more detail by way of examples in which all parts are by weight.

Preparatory Example 1

56.8 g of cysteamine hydrochloride and 50.6 g of triethylamine were dissolved in 500 ml of ethanol, to which was added 148.1 g of an aqueous 25% glyoxylic acid solution. The mixture was refluxed for 1.5 hours, cooled and filtered thereby giving 41.6 g (yield 62.5%) of thiazolidine-2-carboxylic acid. The melting point was 187°-189° C. (decomposed).

6.66 g of thiazolidine-2-carboxylic acid thus obtained and 2.0 g of caustic soda were dissolved in 100 ml of water, to which was added a solution of 9.40 g of 3,5-dichlorophenylisocyanate in 50 ml of chlorobenzene, followed by stirring at room temperature for 2 hours. Then the reaction mixture was extracted with ether and the water layer was neutralized with concentrated hydrochloric acid. The resulting crystals were separated, washed with water and dried to give 14.4 g (yield 89.5%) of 3-(3,5-dichlorophenylcarbamoyl)thiazolidine-2-carboxylic acid. The melting point was found to be 175.5°-177.0° C.

Elementary Analysis: Found (calculated in parentheses): C 40.88% (41.14%), H 3.11% (3.14%), N 8.86% (8.72%), Cl 22.24% (22.08%).

A mixture of 13.0 g of 3-(3,5-dichlorophenylcarbamoyl)thiazolidine-2-carboxylic acid thus obtained and 50 ml of concentrated hydrochloric acid was stirred at 120° C. for 2 hours. Then the reaction mixture was cooled and filtered to separate the precipitate, followed by recrystallization from a mixed solvent of ethyl acetate and n-hexane to give 10.7 g (yield 86.9%) of 6-(3,5-dichlorophenyl)perhydroimidazo[5,1-b]thiazole-5,7-dion (Compound No. 1). Its melting point and Elementary Analysis were as given in table 1.

PREPARATORY EXAMPLE 2

A mixture of 20.0 g of the thiazolidine-2-carboxylic acid obtained in Preparatory Example 1 and 200 ml of a 20% hydrogen chloride ethanol solution was refluxed for 2 hours. The solvent was distilled off under reduced pressure, followed by adding water and neutralizing with an aqueous saturated solution of sodium bicarbonate. After extraction with ethyl acetate, the extract was vacuum distilled to give 19.1 g (yield 79.8%) of thiazolidine-2-carboxylic acid ethyl ester. The boiling point was found to be 104°-105° C./5.5 mmHg.

A mixture of 1.61 g of ethyl thiazolidine-2-carboxylic acid ethyl ester thus obtained, 2.04 g of 3,5-dichlorophenylisothiocyanate and 20 ml of toluene was heated at 90° C. for 1 hour. Then the reaction mixture was cooled and the precipitate was separated by filtration to give 3.11 g (yield 85.1%) of 3-(3,5-dichlorophenylthiocarbamoyl)thiazolidine-2-carboxylic ethyl ester. The melting point was 170.5°-171.5° C. and the results of elementary analysis were as follows: Found (calculated in parentheses): C 42.68% (42.74%), H 3.93% (3.86%), N 7.70% (7.67%), Cl 19.32% (19.41%).

A mixture of 2.19 g of the obtained 3-(3,5-dichlorophenylthiocarbamoyl)thiazolidine-2-carboxylic acid ethyl ester and 20 ml of concentrated hydrochloric acid was stirred at 120° C. for 1.5 hours. After the reaction mixture was cooled, the precipitate was separated, followed by recrystallization from a mixed solvent of ethyl acetate and n-hexane to give 1.43 g (yield 74.7%) of 6-(3,5-dichlorophenyl)perhydroimidazo[5,1-b]thiazole-5-thion-7-on (Compound No. 2). The resulting point and the elementary analysis were as given in table 1.

PREPARATORY EXAMPLE 3

A mixture of 36.6 g of cysteamine hydrochloride, 32.6 g of triethylamine, 32.9 g of methyl pyruvate and 500 ml of ethanol was refluxed for 2 hours. The reaction mixture was concentrated under reduced pressure to afford a residue which was, after addition of water, extracted with ethyl acetate. The extract was vacuum distilled to give 36.6 g (yield 70.4%) of 2-methylthiazolidine-2-carboxylic acid methyl ester with a boiling point of 76° C./2 mmHg.

3.22 g of the thus obtained 2-methylthiazolidine-2-carboxylic acid methyl ester was added to a solution of 0.80 g of caustic soda in 20 ml of water and stirred at room temperature to give an aqueous solution of sodium 2-methylthiazolidine-2-carboxylate. To the solution was added 3.76 g of 3,5-dichlorophenylisocyanate in 20 ml of chlorobenzene, followed by stirring at room temperature for 1.5 hours. Then the reaction mixture was extracted with ether and the water layer was neutralized with concentrated hydrochloric acid. The resulting crystals were separated, washed with water and dried to give 5.22 g (yield 77.9%) of 2-methyl-3-(3,5-dichlorophenylcarbamoyl)thiazolidine-2-carboxylic acid with a melting point of 164°-166° C. The results of the elementary analysis were as follows: Found (calculated in parentheses): C 43.21% (43.00%), H 3.58% (3.61%), N 8.28% (8.36%), Cl 21.28% (21.15%).

5.0 g of the thus obtained 2-methyl-3-(3,5-dichlorophenylcarbamoyl)thiazolidine-2-carboxylic acid and 5 mg of sodium acetate were added to 30 ml of acetic anhydride and heated at 90° C. for 2 hours. The reaction mixture was concentrated under reduced pressure, to which was added water. The resultant crystals were recrystallized from a mixed solvent of ethyl acetate and n-hexane to give 3.92 g of 7a-methyl-6-(3,5-dichlorophenyl)perhydroimidazo[5,1-b]thiazole-5,7-dion (Compound No. 3). The results of the elementary analysis and the melting point were as given in table 1.

PREPARATORY EXAMPLE 4

A mixture of 1.61 g of the 2-methylthiazolidine-2-carboxylic acid methyl ester obtained in Preparatory Example 3, and 2.04 g of 3,5-dichlorophenylisothiocyanate was heated at 90° C. for 2 hours. Then the reaction mixture was concentrated under reduced pressure, followed by recrystallization from a mixed solvent of toluene and n-hexane to give 2.50 g (yield 75.0%) of 7a-methyl-6-(3,5-dichlorophenyl)perhydroimidazo[5,1-b]thiazole-5-thion-7-on (Compound No. 4) with a melting point of 160°-161° C. The results of the elementary analysis and a melting point were as given in table 1.

PREPARATORY EXAMPLE 5

1.52 g of the compound No. 1 obtained in Preparatory Example 1 was dissolved in 10 ml of methylene chloride, to which was added, while ice cooling, 1.04 g of m-chloroperbenzoic acid in 12.5 g of methylene chloride, followed by heating under reflux for 1 hour. Thereafter, 1.04 g of m-chloroperbenzoic acid in 12.5 ml of methylene chloride was again added to the reaction system, which was refluxed for a further 1 hour to complete the reaction. After the reaction solution had been cooled and washed with a dilute caustic acid, the solution was concentrated to afford a residue, which was chromatographed on a column of silica gel with ethylacetate to give 0.50 g (yield 29.8%) of 6-(3,5-dichlorophenyl)perhydroimidazo[5,1-b]thiazole-5,7-dion-1,1-dioxide (Compound No. 5). The results of the elementary analysis and melting point determination as given in table 1.

PREPARATORY EXAMPLE 6

The same procedure of Preparatory Example 5 was repeated except using 1.52 g of the compound No. 3 obtained in Preparatory Example 3 instead of the compound No. 1. After completion of the reaction, the reaction mixture was washed with a dilute caustic soda, concentrated, and then recrystallized from a mixed solvent of ethyl acetate and n-hexane to give 1.18 g (yield 67.6%) of 7a-methyl-6-(3,5-dichlorophenyl)perhydroimidazo[5,1-b]thiazole-5,7-dion-1,1-dioxide (Compound No. 6). The results of the elementary analysis and melting point determination were as given in table 1.

PREPARATORY EXAMPLE 7

11.4 g of cysteamine hydrochloride and 10.1 g of triethylamine were dissolved in 100 ml of ethanol, to which was added 10.2 g of 2-keto-butyric acid. The mixture was refluxed for 30 minutes, cooled and filtered thereby giving 10.6 g (yield 65.7%) of 2-ethyl-thiazolidine-2-carboxylic acid with a melting point of 235°–238° C. (decomposed).

10.0 g of the 2-ethyl-thiazolidine-2-carboxylic acid thus obtained was dissolved in 200 ml of 20% hydrogen chloride-methanol solution. After being refluxed for 30 minutes, the reaction mixture was concentrated under reduced pressure to afford a residue, to which was added water, and was then neutralized with an aqueous saturated solution of sodium bicarbonate. Upon extracting with ethyl acetate, the extract was chromatographed on a column of silica gel to give 2.0 g (yield 18.4%) of 2-ethyl-thiazolidine-2-carboxylic acid methyl ester with a reflex index of $n_D^{26}$ 1.501.

A mixture of 0.62 g of the 2-ethyl thiazolidine-2-carboxylic acid methyl ester thus obtained, 0.66 g of 3,5-dichlorophenyl isocyanate and 10 ml of toluene was stirred at room temperature for 1 hour. Then, the precipitate was filtered to give 1.00 g (yield 77.8%) of 2-ethyl-3-(3,5-dichlorophenylcarbamoyl) thiazolidine-2-carboxylic acid methyl ester with a melting point of 187°–188° C. The results of the elementary analysis were as follows: Found (calculated in parentheses): C 46.48% (46.29%), H 4.35% (4.44%), N 7.50% (7.71%), Cl 19.86% (19.52%).

0.70 g of 2-ethyl-3-(3,5-dichlorophenylcarbamoyl)-thiazolidine-2-carboxylic acid methyl ester was added to 20 ml of 0.1 N sodium methylate-methanol solution, heated at 50° C. for 20 minutes. The reaction mixture was cooled and filtered. The resulting filtrate was 0.16 g (yield 25%) of 7a-ethyl-6-(3,5-dichlorophenyl)perhydroimidazo[5,1-b]thiazole-5,7-dion (compound No. 7). The results of elementary analysis and a melting point were given in table 1.

PREPARATORY EXAMPLE 8

The same procedure of Preparatory Example 7 was repeated except using 2-keto-valeric acid instead of the 2-keto-butyric acid. As the results, the thus obtained compounds corresponding to the starting material were as follows;

2-n-propyl thiazolidine-2-carboxylic acid
m.p. 222°–223° C. (decomposed)

2-n-propyl thiazolidine-2-carboxylic acid methyl ester
m.p. 39°–40° C.

2-n-propyl-3-(3,5-dichlorophenylcarbamoyl)thiazolidine-2-carboxylic acid methyl ester
m.p. 187°–189° C.

Elementary Analysis: Found (calculated in parentheses): C 47.36% (47.75%), H 4.95% (4.81%), N 7.61% (7.42%) Cl 18.53% (18.79%).

7a-n-propyl-6-(3,5-dichlorophenyl)perhydroimidazo[5,1-b]thiazole-5,7-dion (Compound No. 8). The results of elementary analysis and melting point determinations are given in table 1.

PREPARATORY EXAMPLE 9

A mixture of 0.33 g of 2-ethyl thiazolidine-2-carboxylic acid methyl ester obtained in the Preparatory Example 7, 0.38 g of 3,5-dichlorophenyl isothiocyanate and 5 ml of toluene was heated at 90° C. for 2 hours and then concentrated to afford a residue, which was chromatographed on a column of silica gel to give 0.15 g of 7a-ethyl-6-(3,5-dichlorophenyl)perhydroimidazo[5,1-b]thiazole-5-thion-7-on (Compound No. 9). The results of elementary analysis and the melting point determination were as given in table 1.

PREPARATORY EXAMPLE 10

The procedure of Preparatory Example 9 was repeated except using 3-n-propyl thiazolidine-2-carboxylic acid methyl ester obtained in Preparatory Example 8 instead of 2-ethyl thiazolidine-2-carboxylic acid methyl ester to give 7a-n-propyl-6-(3,5-dichlorophenyl)perhydroimidazo[5,1-b]thiazole-5-thion-7-on (Compound No. 10). The results of elementary analysis and the melting point determination are given in table 1.

TABLE 1

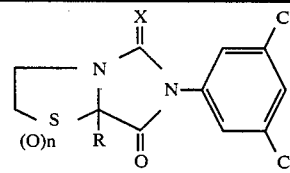

| Compound No. | Substituent R | X | n | Melting Point (°C.) | Elementary Analysis (Found) (Calculated) C (%) | H (%) | N (%) | Cl (%) |
|---|---|---|---|---|---|---|---|---|
| 1 | H | O | 0 | 141–142 | 43.40 | 2.73 | 9.18 | 22.25 |
|   |   |   |   |   | 43.58 | 2.66 | 9.24 | 23.39 |
| 2 | H | S | 0 | 149.5–150.5 | 41.33 | 2.59 | 8.60 | 22.51 |
|   |   |   |   |   | 41.39 | 2.53 | 8.78 | 22.21 |
| 3 | CH$_3$ | O | 0 | 110–112 | 45.56 | 3.09 | 8.72 | 22.20 |
|   |   |   |   |   | 45.44 | 3.18 | 8.83 | 22.35 |
| 4 | CH$_3$ | S | 0 | 160–161 | 43.36 | 2.59 | 8.36 | 21.41 |
|   |   |   |   |   | 43.25 | 3.02 | 8.41 | 21.28 |
| 5 | H | O | 2 | 176–178 | 40.01 | 2.36 | 8.27 | 21.35 |

TABLE 1-continued

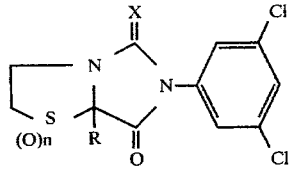

| Compound No. | Substituent R | X | n | Melting Point (°C.) | Elementary Analysis (Found) (Calculated) | | | |
|---|---|---|---|---|---|---|---|---|
| | | | | | C (%) | H (%) | N (%) | Cl (%) |
| 6 | CH$_3$ | O | 2 | 190–191 | 39.42 | 2.41 | 8.36 | 21.16 |
| | | | | | 41.35 | 2.95 | 7.89 | 20.13 |
| | | | | | 41.28 | 2.89 | 8.02 | 20.31 |
| 7 | C$_2$H$_5$ | O | 0 | 138–139 | 46.99 | 3.78 | 8.22 | 21.41 |
| | | | | | 47.14 | 3.65 | 8.46 | 21.41 |
| 8 | n-C$_3$H$_7$ | O | 0 | 145.5–146.5 | 48.34 | 4.08 | 7.83 | 20.28 |
| | | | | | 48.70 | 4.09 | 8.11 | 20.54 |
| 9 | C$_2$H$_5$ | S | 0 | 139–140 | 44.70 | 3.55 | 8.16 | 20.12 |
| | | | | | 44.96 | 3.48 | 8.07 | 20.42 |
| 10 | n-C$_3$H$_7$ | S | 0 | 153–153.5 | 46.81 | 3.90 | 7.91 | 19.78 |
| | | | | | 46.54 | 3.91 | 7.75 | 19.62 |

PREPARATION EXAMPLE 1

50 parts of the compound No. 1, 45 parts of talc, and 5 parts of Sorpol 8070 (trade name, surface active agent comprised principally of higher alcohol sulfate) were uniformly milled and mixed to give a fungicide (wettable powder).

PREPARATION EXAMPLE 2

40 parts of the compound No. 3, 10 parts of white carbon, 47 parts of diatomaceous earth, and 3 parts of Sorpol 5039 (trade name, surface active agent comprised principally of polyoxyethylene alkyl aryl ether sulfonate) were uniformly milled and mixed to give a fungicide (wettable powder).

PREPARATION EXAMPLE 3

30 parts of the compound No. 2, 15 parts of Sorpol 3005X (trade name, a mixture of a nonionic surface active agent and an anionic surface active agent), 25 parts of xylene and 30 parts of dimethylformamide were mixed and dissolved to give a fungicide (emulsion).

PREPARATION EXAMPLE 4

2 parts of the compound No. 4 and 98 parts of N,N-kaolin clay (product of Tsuchiya Kaolin Co., Ltd.) were mixed and powdered to give a fungicide (dust).

TEST EXAMPLE 1

Preventive test against Cucumber Gray Mold disease

Cucumber plants (cultivar: Satsukimidori), were each grown in a 15 cm$\phi$ plastic pot to the first leaf stage. The plants were sprayed with 10 ml/1 pot of aqueous diluted suspensions of various types of wettable powders (including the wettable powder containing, as its active ingredient, compound No. 1 obtained in the Preparation Example 1, wettable powders, containing as active ingredients compounds Nos. 2–10 obtained in a manner similar to Preparation Example 1, and a wettable powder for a comparison chemical containing, as its active ingredient, tetrachloroisophthalonitrile obtained in manner similar to Preparation Example 1). After air-drying for 5 hours, the plants were inoculated with the mecelia of *Botrytis cinerea* inoculated with shaking in Yeast-Glucose liquid medium.

The cucumbers were kept in the humidic chamber at 23° C. for 4 days after inoculation and then checked with respect to their disease index. The checking was conducted as follows: The leaves were checked to determine the extent of lesion area and classified into six groups as indicated by indices 0, 1, 2, 3, 4, 5 based on the extent of the lesions and on the numbers of leaves $n_0$, $n_1$, $n_2$, $n_3$, $n_4$, and $n_5$ which corresponded to the indices, respectively, were also determined to calculate the disease index from the following equation. The results are shown in Table 2 below.

| Disease Index | Lesion Area |
|---|---|
| 0 | no lesion |
| 1 | lesion area of 1/5 times the total leaf area |
| 2 | lesion area of 2/5 times the total leaf area |
| 3 | lesion area of 3/5 times the total leaf area |
| 4 | lesion area of 4/5 times the total leaf area |
| 5 | lesion area above 4/5 times the total leaf area |

Disease severity index =
$$\frac{0 \times n_0 + 1 \times n_1 + 2 \times n_2 + 3 \times n_3 + 4 \times n_4 + 5 \times n_5}{n}$$

(where n is the total number of checked leaves)

The preventive value was calculated from the following equation.

Preventive Value (%) =
$$\frac{(A) - \text{Disease severity index treated}}{\text{Disease severity index untreated }(A)} \times 100$$

TABLE 2

| Compound No. | Substituent R | X | n | Concentration (ppm) | Preventive Value (%) |
|---|---|---|---|---|---|
| 1 | H | O | 0 | 500 | 100 |
| | | | | 250 | 100 |
| | | | | 125 | 100 |
| | | | | 62.5 | 100 |
| 2 | H | S | 0 | 500 | 92 |
| | | | | 500 | 100 |
| 3 | CH$_3$ | O | 0 | 250 | 100 |
| | | | | 125 | 100 |
| | | | | 62.5 | 100 |
| 4 | CH$_3$ | S | 0 | 500 | 93 |
| 5 | H | O | 2 | 500 | 91 |
| 6 | CH$_3$ | O | 2 | 500 | 90 |
| 7 | C$_2$H$_5$ | O | 0 | 500 | 100 |
| 8 | n-C$_3$H$_7$ | O | 0 | 500 | 97 |
| 9 | C$_2$H$_5$ | S | 0 | 500 | 96 |
| 10 | n-C$_3$H$_7$ | S | 0 | 500 | 94 |
| Comparison* | | | | 500 | 65 |
| Un-treated | | | | — | 0 |

*Comparison Chemical
Tetrachloro isophthalonitrile

TEST EXAMPLE 2

Preventive test against Rice brown spot disease

Rice plants (cultivar: Kinmaze) were each grown in a 10 cm$\phi$ porcelain pot to the 3-4 leaves stage. The plants were sprayed with 10 ml/1 pot of aqueous diluted suspensions of various types of wettable powders of the chemicals of the invention and comparison chemical [bis(dimethyl thiocarbamoyl)disulfide]. The wettable powders were prepared in a manner similar to test example 1.

After air drying for 5 hours, the plants were inoculated with a spore suspension of *Cochliobolus miyabeans* incubated with a chaffy medium at 25° C. for 5 days.

These plants were kept in the humidic chamber at 27° C. for 48 hours after inoculation and the number of lesions were counted and preventive value was calculated according to the following equation.

Preventive value (%)

$$\frac{(A) - \text{number of lesions treated}}{\text{number of lesions untreated } (A)} \times 100$$

The results are given in Table 3.

TABLE 3

$$\begin{array}{c}\text{structure with X, Cl, N, S, (O)n, R, O, Cl substituents}\end{array}$$

| Compound No. | Substituent R | X | n | Concentration (ppm) | Preventive Value (%) |
|---|---|---|---|---|---|
| 1 | H | O | 0 | 500 | 95.1 |
| 2 | H | S | 0 | 500 | 88.4 |
| 3 | CH$_3$ | O | 0 | 500 | 96.2 |
| 4 | CH$_3$ | S | 0 | 500 | 85.7 |
| 5 | H | O | 2 | 500 | 89.6 |
| 6 | CH$_3$ | O | 2 | 500 | 90.6 |
| 7 | C$_2$H$_5$ | O | 0 | 500 | 90.8 |
| 8 | n-C$_3$H$_7$ | O | 0 | 500 | 85.4 |
| 9 | C$_2$H$_5$ | S | 0 | 500 | 82.9 |
| 10 | n-C$_3$H$_7$ | S | 0 | 500 | 83.2 |
| Comparison* | | | | 500 | 83.3 |
| Un-treated | | | | — | 0 |

*Comparison chemical Bis(dimethyl thiocarbamoyl)disulfide

TEST EXAMPLE 3

Preventive test against kidney bean stem rot

Kidney bean plants (cultivar: Kintoki) were each grown in a 15 cm$\phi$ plastic pot to the trifoliate stage. The plants were sprayed with 10 ml/1 pot of an aqueous diluted suspension of wettable powders of the chemicals of the invention and comparison chemical.

The wettable powders were prepared in a manner similar to example 1. After air drying for 5 hours, the plants were inoculated with mecelia of *Sclerotinia sclerotiorum* incubated with shaking in a Yeast-Glucose liquid medium, and kept in a humidic chamber at 25° C. for 4 days. Then the preventive value was calculated according to the equation given in test example 1. The results are given in table 4.

TABLE 4

| Compound No. | Concentration (ppm) | Preventive Value (%) |
|---|---|---|
| | 200 | 100 |

TABLE 4-continued

| Compound No. | Concentration (ppm) | Preventive Value (%) |
|---|---|---|
| No. 1 | 100 | 98.2 |
| | 50 | 95.3 |
| | 200 | 100 |
| No. 2 | 100 | 96.5 |
| | 50 | 93.8 |
| Comparison* | 500 | 70.5 |
| Un-treated | — | 0 |

*Comparison chemical 2,6-dichloro-4-nitroaniline

Antifungal Test

Each chemical was mixed with PDA medium in an amount enough to obtain the pre-determined concentration level and solidified in 9 cm$\phi$ Petri dish. Then, various plant disease fungi were inoculated on the middle of the mixed agar plate and cultured at 25° C. for 4 days.

The minimum inhibition concentration (MIC) means that at which the development of the inoculated fungus was not recognized with the naked eye.

The results are given in Table 5.

TABLE 5

| | MIC Concentration (ppm) | | |
|---|---|---|---|
| | Compd. No. | | |
| Tested Fungi | No. 1 | No. 3 | Comparison** |
| Botrytis cinerea (strain I) | 3.1 | 1.6 | 0.4 |
| Botrytis cinerea (strain II*) | 3.1 | 0.8 | >100 |
| Sclerotinia sclerotiorum | 1.6 | 1.6 | |
| Altrenaria mali | 3.1 | 3.1 | >100 |
| Altrenaria Kikuchiana | 3.1 | 3.1 | >100 |
| Botrytis allii | 6.2 | 3.1 | |

*Botrytis cinerea (strain II) is the strain resistant to benzoimidazole-type fungicide e.g. Benlate, Topsin-M.
**Comparison chemical is Benlate.

What claimed is:

1. 6-(3,5-dichlorophenyl)-perhydroimidazo[5,1-b]thiazole compound represented by the formula (1)

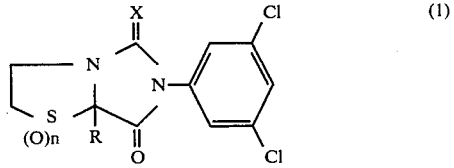

(1)

wherein, R represents hydrogen atom or an alkyl group of 1 through 4 carbon atoms, X represents an oxygen atom or a sulfur atom and n represents 0, 1 or 2.

2. 6-(3,5-dichlorophenyl)perhydroimidazo[5,1-b]thiazole compound of claim 1, wherein n represents zero.

3. 6-(3,5-dichlorophenyl)perhydroimidazo[5,1-b]thiazole compound of claim 1, wherein X represents an oxygen atom and n represents zero.

4. 6-(3,5-dichlorophenyl)perhydroimidazo[5,1-b]thiazole-5,7-dione.

5. 7a-methyl-6-(3,5-dichlorophenyl)perhydroimidazo[5,1-b]thiazole-5,7-dion.

6. A method of controlling fungal infection on plants which comprises applying to said plants an antifungal effective amount of a compound of the formula

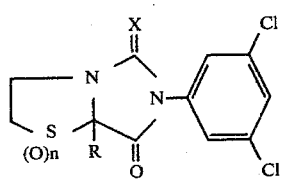

wherein, R represents hydrogen atom or an alkyl group of 1 through 4 carbon atoms, X represents oxygen atom or sulfur atom and n represents 0, 1 or 2.

7. A method according to claim 6, wherein n represents zero and X represents an oxygen atom.

8. A method according to claim 6, wherein said compound is 6-(3,5-dichlorophenyl)perhydroimidazo[5,1-b]thiazole-5,7-dione.

9. A method according to claim 6, wherein said compound is 7a-methyl-6-(3,5-dichlorophenyl)perhydroimidazo[5,1-b]thiazole-5,7-dione.

* * * * *

UNITED STATES PATENT AND TRADEMARK OFFICE
CERTIFICATE OF CORRECTION

PATENT NO. : 4,229,461
DATED : October 21, 1980
INVENTOR(S) : SHIGEMATSU et al

It is certified that error appears in the above-identified patent and that said Letters Patent are hereby corrected as shown below:

In the abstract, line 3, delete "derivative".

Col. 1, line 13, "-5-thion-7-ons" should read --- -5-thione-7-ones---;

line 25, "5,7-dions" should read --- 5,7- diones ---;

line 27, "thion-7-ons" should read ---thione-7-ones---.

Col. 2, line 4, "ethy" should read ---ethyl---;

line 9, "of" should read ---or---;

line 11, "fruits-trees" should read ---fruit-trees---;

line 31, "dion" should read ---dione---;

line 32, "-5,7-dion" should read --- -5,7-dione ---.

Col. 3, line 44, "-5,7-dions" should read --- -5,7-diones---;

line 46, "5-thion-7-ons" should read ---5-thione-7-ones-

UNITED STATES PATENT AND TRADEMARK OFFICE
CERTIFICATE OF CORRECTION

PATENT NO. : 4,229,461
DATED : October 21, 1980
INVENTOR(S) : SHIGEMATSU et al

It is certified that error appears in the above—identified patent and that said Letters Patent are hereby corrected as shown below:

Col 3, line 63, "5,7-dions" should read ---5,7-diones---;

line 64, "-5-thion-7-ons" should read --- -5-thione-7-ones---.

Col. 4, line 9, "5,7-dion-1-oxides" should read ---5,7-dione-1-oxides---;

line 10, "-5-thion-7-on-1" should read --- -5-thione-7-one-1- ---.

Col. 5, line 50, "dion" should read ---dione---.

Col. 6, line 15, "5-thion-7-on" should read ---5-thione-7-one---;

line 53, "-5,7-dion" should read ---5,7-dione---;

line 66, "-5-thion-7-on" should read --- -5-thione-7-one-

Col. 7, line 12, "acid" should read --- soda---;

UNITED STATES PATENT AND TRADEMARK OFFICE
CERTIFICATE OF CORRECTION

PATENT NO. : 4,229,461
DATED : October 21, 1980
INVENTOR(S) : SHIGEMATSU et al

It is certified that error appears in the above-identified patent and that said Letters Patent are hereby corrected as shown below:

Col. 7, line 17, "dion-" should read ---dione- ---;

line 18, "as" should read ---were as---;

line 30, "-5,7-dion-" should read --- -5,7-dione- ---.

Col. 8, line 3, "-5,7-dion" should read --- -5,7-dione---;

line 5, "were" should read ---were as---;

line 10, "As the results, the thus obtained" should read ---As a result the following---;

line 11, "were" should read ---were obtained---;

line 12, the ";" should be ---:---;

line 24, "-5,7-dion" should read --- -5,7-dione---;

line 36, "-5-thion-7-on" should read --- -5-thione-7-one line 46, "-5-thion-7-on" should read --- -5-thione-7-one

UNITED STATES PATENT AND TRADEMARK OFFICE
CERTIFICATE OF CORRECTION

PATENT NO. : 4,229,461
DATED : October 21, 1980
INVENTOR(S) : SHIGEMATSU et al

It is certified that error appears in the above—identified patent and that said Letters Patent is hereby corrected as shown below:

In Table 1, under the subheading "H" the 7th listed value "2.59" should read ---2.95---.

Col. 10, line 1, "mecelia" should read ---mycelia---.

Table 2, the data for compounds 1,2,3 and 4 should be distinguished by lines of demarcation between each group as follows

| COMPOUND NO. | SUBSTITUENT R | X | n | CONCENTRATION (ppm) | PREVENTIVE VALUE (%) |
|---|---|---|---|---|---|
| 1 | H | O | 0 | 500　　250　　125　　62.5 | 100　　100　　100　　100 |
| 2 | H | S | 0 | 500　　500 | 92　　100 |
| 3 | $CH_3$ | O | 0 | 250　　125　　62.5 | 100　　100　　100 |
| 4 | $CH_3$ | S | 0 | 500 | 93 |

UNITED STATES PATENT AND TRADEMARK OFFICE
CERTIFICATE OF CORRECTION

PATENT NO. : 4,229,461

DATED : October 21, 1980

INVENTOR(S) : SHIGEMATSU et al

It is certified that error appears in the above—identified patent and that said Letters Patent is hereby corrected as shown below:

Col 11, line 9, the second closed ")" should be a closed bracket --- ---;

line 58, "mecelia" should read ---mycelia---.

Col. 12, Table 4-continued, the data for the compounds should be distinguished as follows:

| COMPOUND No. | CONCENTRATION (ppm) | PREVENTIVE VALUE (%) |
|---|---|---|
| No. 1 | 100 | 98.2 |
|  | 50 | 95.3 |
|  | 200 | 100 |
| No. 2 | 100 | 96.5 |
|  | 50 | 93.8 |
| Comparison* | 500 | 70.5 |
| Untreated | ---- | 0 |

UNITED STATES PATENT AND TRADEMARK OFFICE
CERTIFICATE OF CORRECTION

PATENT NO. : 4,229,461
DATED : October 21, 1980
INVENTOR(S) : SHIGEMATSU et al

It is certified that error appears in the above-identified patent and that said Letters Patent are hereby corrected as shown below:

Col. 12, Table 5, the 4th listed fungus "Altrenaria" should read ---Alternaria---;

the 5th listed fungus "Altrenaria" should read ---Alternaria---.

Claim 5, line 2,"-dion" should read-- -dione---.

Signed and Sealed this

Twenty-first Day of April 1981

[SEAL]

Attest:

RENE D. TEGTMEYER

Attesting Officer    Acting Commissioner of Patents and Trademarks